US008227248B2

(12) United States Patent
Kikuchi et al.

(10) Patent No.: US 8,227,248 B2
(45) Date of Patent: Jul. 24, 2012

(54) COMPOSITION FOR NUCLEIC-ACID TRANSFECTION

(75) Inventors: Hiroshi Kikuchi, Koto-ku (JP); Hideo Kobayashi, Edogawa-ku (JP); Kouichi Hashimoto, Yachiyo (JP); Ayako Iijima, Fukuyama (JP); Daigo Asano, Koto-ku (JP)

(73) Assignee: Hokkaido System Science Co., Ltd., Sapporo-shi (JP)

( * ) Notice: Subject to any disclaimer, the term of this patent is extended or adjusted under 35 U.S.C. 154(b) by 619 days.

(21) Appl. No.: 12/306,620

(22) PCT Filed: Jun. 29, 2007

(86) PCT No.: PCT/JP2007/000720
§ 371 (c)(1),
(2), (4) Date: Dec. 24, 2008

(87) PCT Pub. No.: WO2008/001505
PCT Pub. Date: Jan. 3, 2008

(65) Prior Publication Data
US 2009/0239222 A1 Sep. 24, 2009

(30) Foreign Application Priority Data

Jun. 30, 2006 (JP) ................................. 2006-182510

(51) Int. Cl.
*C12N 15/88* (2006.01)
(52) U.S. Cl. ........ 435/458; 424/450; 514/44 R; 562/573
(58) Field of Classification Search .......................... None
See application file for complete search history.

(56) References Cited

U.S. PATENT DOCUMENTS

| 5,744,159 A | 4/1998 | Yagi et al. |
| 6,372,714 B1 | 4/2002 | Tanaka et al. |
| 7,091,018 B2 * | 8/2006 | Fujiwara et al. ............... 435/193 |
| 7,906,625 B2 * | 3/2011 | Shen et al. .................. 530/387.3 |
| 2004/0072769 A1 * | 4/2004 | Yin ................................. 514/44 |

FOREIGN PATENT DOCUMENTS

| EP | 0 475 178 A1 | 3/1992 |
| EP | 0 795 325 A1 | 9/1997 |
| JP | 6 200336 | 7/1984 |
| JP | 2-135092 | 5/1990 |
| JP | 9-248182 | 9/1997 |

OTHER PUBLICATIONS

Mizuno, M. et al., "Cationic liposomes conjugation to recombinant adenoviral vectors containing herpes simplex virus thymidine kinase gene followed by ganciclovir treatment reduces viral antigenicity and maintains antitumor activity in mouse experimental glioma models", Cancer Gene Therapy, vol. 9, pp. 825-829, (2002).
Watarai, T. S. et al., "In Vivo Antitumor Effect of Cationic Liposomes Containing Diphtheria Toxin A-Chain Gene on Cells Infected with Bovine Leukemia Virus", J Vet Med Sci., vol. 59, No. 7, pp. 617-6129, (1997).
Goto, M. et al., "Design of Surfactants Suitable for Surfactant-Coated Enzymes As Catalysts in Organic Media", Department of Chemical Science & Technology, vol. 26, No. 1, pp. 109-111, (1993).
Takashi Harigai, et al., "Preferential Binding of Polyethylene Glycol-Coated Liposomes Containing a Novel Cationic Lipid, TRX-20, to Human Subendthelial Cells via Chondroitin Sulfate", Pharmaceutical Research, vol. 18, No. 9, Sep. 2001, pp. 1284-1290.
H. Arima, et al., "Effects of Oligodeoxynucleotides on the Physicochemical Characteristics and Cellular Uptake of Liposomes", J Pharm Sci., vol. 86, No. 4, Apr. 1997 pp. 438-442 (Abstract only).
M. A. Maslov, et al., "Cationic Amphiphiles of Both Lipid and Nonlipid Nature in Gene Therapy", Russian Chemical Bulletin, vol. 49, No. 3, Mar. 2000, pp. 385-401.
L. I. Patrushev, et al. "Expression of Genes", Publishing House Mir, vol. 1, 2004, pp. 149-154.
Office Action issued Apr. 7, 2011 in Russian Patent Application No. 2009103003/10(003879) (with English translation).
Office Action issued Aug. 11, 2010, in China Patent Application No. 200780024080.2. Dan-Dan Zhao, et al., "Gene transfection by cationic liposomes: comparison of the transfection efficiency of liposomes prepared from various positively charged lipids", Acta Med Okayama, vol. 51, Issue 3, Article 6, Jun. 1997, pp. 149-154.
Michael J. Bennett, et al., "Cholesterol Enhances Cationic Liposome-Mediated DNA Transfection of Human Respiratory Epithelial Cells", Bioscience Reports, vol. 15, No. 1, 1995, pp. 47-53.
Ryosuke Okayama, et al., "Cationic cholesterol with a hydroxyethylamino head group promotes significantly liposome-mediated gene transfection", FEBS Letters, 408, 1997, pp. 232-234.
C. Ropert, "Liposomes as a gene delivery system", Brazilian Journal of Medical and Biological Research, 32, 1999, pp. 163-169.
Supplementary Search Report issued Oct. 29, 2010 in European Patent Application No. 07790240.1-2404/2034019.
Japanese Office Action as received in the corresponding Japanese Patent Application No. 2008-522307 dated May 22, 2012.
Proceedings of the Annual Meeting of the Pharmaceutical Society of Japan, Mar. 6, 2006, vol. 126, P131, P30[S]am-532 w/English Translation.

* cited by examiner

*Primary Examiner* — Jim Ketter
(74) *Attorney, Agent, or Firm* — Oblon, Spivak, McClelland, Maier & Neustadt, L.L.P.

(57) ABSTRACT

To provide a nucleic-acid-transfecting composition which exhibits low cytotoxicity, which facilitates a nucleic acid transfection into cells, and which improves expression of the nucleic acid in the cells. The invention provides a composition for transfecting a nucleic acid into a cell, including a compound represented by the following formula (I) (wherein each of $R^1$ and $R^2$, which are identical to or different from each other, represents a saturated or unsaturated hydrocarbon group; $R^3$ represents a $C_{1-6}$ alkyl group or a $C_{1-6}$ hydroxyalkyl group; m is an integer from 1 to 10; and X represents a halogen atom), and a phospholipid.

$$R^1-O-\overset{O}{\underset{\underset{\underset{R^2-O-C}{|}}{(CH_2)}}{C}}-CH-NH-\overset{O}{C}-(CH_2)_m-\overset{CH_3}{\underset{CH_3}{\underset{|}{N^+}}}-R^3 \quad X^- \quad (I)$$

14 Claims, No Drawings

SEQUENCE LISTING

<160> NUMBER OF SEQ ID NOS: 4

<210> SEQ ID NO 1
<211> LENGTH: 27
<212> TYPE: RNA
<213> ORGANISM: Artificial Sequence
<220> FEATURE:
<223> OTHER INFORMATION: Synthetic Construct

<400> SEQUENCE: 1
acaucacgua cgcggaauac uucgaag    27

<210> SEQ ID NO 2
<211> LENGTH: 27
<212> TYPE: RNA
<213> ORGANISM: Artificial Sequence
<220> FEATURE:
<223> OTHER INFORMATION: Synthetic Construct

```
<400> SEQUENCE: 2
uauguagugc augcgccuua ugaagcu                                              27

<210> SEQ ID NO 3
<211> LENGTH: 27
<212> TYPE: RNA
<213> ORGANISM: Artificial Sequence
<220> FEATURE:
<223> OTHER INFORMATION: Synthetic Construct

<400> SEQUENCE: 3
acaucacuua cgcugaguac uucgaag                                              27

<210> SEQ ID NO 4
<211> LENGTH: 27
<212> TYPE: RNA
<213> ORGANISM: Artificial Sequence
<220> FEATURE:
<223> OTHER INFORMATION: Synthetic Construct

<400> SEQUENCE: 4
uauguaguga augcgacuca ugaagcu                                              27
```

COMPOSITION FOR NUCLEIC-ACID TRANSFECTION

CROSS-REFERENCE TO RELATED APPLICATIONS

The present application is a 35 U.S.C. §371 National Stage patent application of International patent application PCT/JP2007/000720, filed on Jun. 29, 2007, which claims priority to Japanese patent application JP 2006-182510, filed on Jun. 30, 2006.

TECHNICAL FIELD

The present invention relates to a composition for a nucleic acid transfection into cells (hereinafter may be referred to as a "nucleic-acid-transfecting composition").

BACKGROUND ART

For a nucleic acid (e.g., a gene) transfection, there have already been known methods which make use of cationic lipid alone, or a complex formed between the nucleic acid and liposomes containing cationic lipid (see, for example, Patent Document 1). In such a method, commercially available reagents such as "Lipofectamine," "Lipofectin," "Transfectam," "Genetransfer," and "Lipofectamine 2000" are employed.

However, these commercially available reagents pose problems as described below. (a) Such a commercially available reagent exhibits poor storage stability, or fails to attain intracellular transfection and expression of a gene by use of, for example, liposomes at high reproducibility. (b) Such a commercially available reagent is very unstable in serum (fetal bovine serum) added to a medium for cell culture, and thus the reagent requires an intricate process for a nucleic acid transfection (i.e., a serum-containing medium in which cells are cultured is temporarily replaced with a serum-free medium, and then the serum-free medium is replaced with the serum-containing medium after a nucleic acid transfection). Recently, it has been elucidated that such a commercially available reagent is very unstable also in blood or a living body. (c) Most of these commercially available reagents (e.g., Lipofectamine, Lipofectin, and Lipofectamine 2000) are provided only in the form of a dispersion containing lipid dispersed in water. Therefore, an aqueous solution of a gene is added to such a reagent for transfecting the gene into cells. However, in such a case, liposomes encapsulating the gene fail to be produced, although a complex in which the gene is bound to the outside of liposomes can be produced. Lipofectamine 2000 should not be excessively stirred or shaken and must be handled with the greatest care for preventing formation of cationic lipid peroxide. (d) Such a commercially available reagent exhibits very potent cytotoxicity.

Thus, many problems are involved in some commercially available reagents for a nucleic acid (e.g., a gene) transfection by use of cationic lipid singly or cationic-lipid-containing liposomes.

Patent Document 1: JP-A-1990-135092

DISCLOSURE OF THE INVENTION

Problems to be Solved by the Invention

An object of the present invention is to provide a nucleic-acid-transfecting composition which exhibits low cytotoxicity, which facilitates a nucleic acid transfection into cells, and which improves expression of the nucleic acid in the cells.

Means for Solving the Problems

The present inventors have conducted extensive studies on means for achieving low cytotoxicity, facilitating a nucleic acid transfection into cells, and improving expression of the nucleic acid in the cells, and as a result have found that when a compound represented by the following formula (I):

[F1]

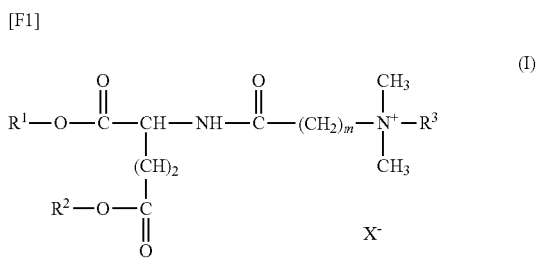

(wherein each of $R^1$ and $R^2$, which are identical to or different from each other, represents a $C_{12-22}$ saturated or unsaturated hydrocarbon group; $R^3$ represents a $C_{1-6}$ alkyl group or a $C_{1-6}$ hydroxyalkyl group; m is an integer from 1 to 10; and X represents a halogen atom), a phospholipid, and a nucleic acid (e.g., a gene) are administered to a subject in need thereof or applied to cells, low cytotoxicity is achieved, and the nucleic acid is effectively transfected into the cells. The present invention has been accomplished on the basis of this finding.

Accordingly, the present invention provides the following.

(1) A composition for transfecting a nucleic acid into a cell, comprising a compound represented by formula (1) and a phospholipid.

(2) A composition as described in (1), which further contains cholesterol and/or cholestanol in an amount of 0 to 50 mole on the basis of the total lipid content of the composition.

(3) A composition as described in (1) or (2), wherein the amount of the compound represented by formula (I) is 40 to 60 mol % on the basis of the total lipid content of the composition.

(4) A composition as described in any one of (1) to (3), wherein the ratio by mole of the compound represented by formula (I) to the phospholipid is 2:3 to 16:1.

(5) A composition as described in any one of (1) to (4), wherein, in formula (I), each of $R^1$ and $R^2$ is a $C_{12-18}$ alkyl group or alkenyl group; $R^3$ is a methyl group; and m is 1.

(6) A composition as described in any one of (1) to (5), wherein, in formula (I), X is a chlorine atom or a bromine atom.

(7) A composition as described in any one of (1) to (6), wherein the phospholipid is one or more species selected from among phosphatidylethanolamine, phosphatidylcholine, phosphatidylserine, phosphatidylinositol, phosphatidylglycerol, cardiolipin, sphingomyelin, plasmalogen, and phosphatidic acid.

(8) A composition as described in any one of (1) to (6), wherein the phospholipid is phosphatidylethanolamine.

(9) A composition as described in any one of (1) to (6), wherein the phospholipid is dioleoylphosphatidylethanolamine.

(10) A composition for transfecting a nucleic acid into a cell, comprising N-(α-trimethylammonioacetyl)-dioleyl-D-glutamate chloride, dioleoylphosphatidylethanolamine, and cholesterol.

(11) A composition as described in any one of (1) to (10), which further contains a nucleic acid.
(12) A composition as described in (11), wherein the nucleic acid is a short oligonucleotide.
(13) A composition as described in any one of (1) to (12), which is in the form of a lipid membrane structure.
(14) A composition as described in any one of (1) to (13), which is in the form of a liposome.
(15) A composition as described in any one of (1) to (14), which is a lyophilized product.
(16) A method for transfecting a nucleic acid into a cell, comprising applying a composition as recited in any one of (11) to (15) to a cell in vitro or in vivo.
(17) Use of a composition as recited in any one of (1) to (15) for producing a nucleic-acid-transfecting agent.
(18) A screening method for selecting a substance which increases or inhibits expression of a target nucleic acid, comprising the following steps (i) to (iii):
(i) a step of bringing a test substance into contact with a cell into which a target nucleic acid has been transfected;
(ii) a step of determining the level of expression of the target nucleic acid in the cell which has been brought into contact with the test substance; and
(iii) a step of selecting a test substance showing an expression level as determined in (ii) above that is higher or lower than the level of expression of the target nucleic acid in a control cell, wherein transfection of the target nucleic acid into the cell and/or exposure of the cell to the test substance is carried out by use of a composition as recited in any one of (1) to (15).

Effects of the Invention

The composition of the present invention exhibits low cytotoxicity and realizes an effective nucleic acid transfection into cells. Therefore, the composition of the present invention is useful as a nucleic-acid-transfecting reagent or drug.

BEST MODES FOR CARRYING OUT THE INVENTION

The nucleic-acid-transfecting composition of the present invention is employed together with a nucleic acid which is to be transfected into cells (hereinafter the nucleic acid may be referred to as a "nucleic acid of interest"). No particular limitation is imposed on the composition, so long as it contains at least a compound represented by formula (I) and a phospholipid. The composition of the present invention includes a composition containing a nucleic acid of interest (i.e., a nucleic-acid-containing composition) and a composition containing no nucleic acid of interest.

Now will be described substituents of the compound represented by formula (I) contained in the composition of the present invention.

In formula (I), each of $R^1$ and $R^2$, which are identical to or different from each other, represents a $C_{12-22}$ saturated or unsaturated hydrocarbon group. Specific examples of the hydrocarbon group include a dodecyl group, a tridecyl group, a tetradecyl group, a pentadecyl group, a hexadecyl group, a heptadecyl group, an octadecyl group, an oleyl group, a linoleyl group, and a linolenyl group. Preferably, $R^1$ and $R^2$ are identical to each other. In formula (I), $R^1$ or $R^2$ is preferably a $C_{12-18}$ alkyl or alkenyl group. Specific examples of preferred $C_{12-18}$ alkyl and alkenyl groups include a dodecyl group, a tetradecyl group, a hexadecyl group, an octadecyl group, and an oleyl group. In the present invention, a $C_{12-18}$ alkenyl group is more preferred.

$R^3$ represents a $C_{1-6}$ alkyl group or a $C_{1-6}$ hydroxyalkyl group. Examples of the $C_{1-6}$ alkyl group include a methyl group and an ethyl group. Of these, a methyl group is preferred. Examples of the $C_{1-6}$ hydroxyalkyl group include a hydroxymethyl group and a hydroxyethyl group.

In formula (I), m is an integer from 1 to 10 and is preferably 1 or 10.

X represents a halogen atom such as a chlorine atom or a bromine atom.

The compound represented by formula (I) contained in the composition of the present invention is a known compound and may be produced through a known method (see, for example, JP-A-1994-200336). Alternatively, the compound may be a commercially available product; for example, a product of Sogo Pharmaceutical Co., Ltd., such as N-(α-trimethylammonioacetyl)-didodecyl-D-glutamate chloride (product name: DC-3-12D), N-(α-trimethylammonioacetyl)-didodecyl-L-glutamate chloride (product name: DC-3-12L), N-(α-trimethylammonioacetyl)-dioctadecyl-D-glutamate chloride (product name: DC-3-18D), N-ω-trimethylammoniodecanoyldihexadecyl-D-glutamate bromide (product name: DC-12-16D), and N-ω-trimethylammoniodecanoyldihexadecyl-L-glutamate bromide (product name: DC-12-16L). In the present invention, an N-(α-trimethylammonioacetyl)-dioleyl-glutamate halide is preferred, with N-(α-trimethylammonioacetyl)-dioleyl-D-glutamate chloride being particularly preferred.

The amount of the compound represented by formula (I) contained in the composition of the present invention may be appropriately determined on the basis of the total lipid content of the composition of the present invention. However, the amount of the compound is preferably 20 to 80 mol %, more preferably 40 to 60 mol %, on the basis of the total lipid content of the composition.

Examples of the phospholipid contained in the composition of the present invention include phosphatidylethanolamine, phosphatidylcholine, phosphatidylserine, phosphatidylinositol, phosphatidylglycerol, cardiolipin, sphingomyelin, plasmalogen, and phosphatidic acid. These phospholipids may be employed singly or in combination of two or more species.

More preferably, phosphatidylethanolamine or phosphatidylcholine is employed singly, or these are employed in combination. Particularly preferably, phosphatidylethanolamine is employed. No particular limitation is imposed on the fatty acid group of such a phospholipid, and the fatty acid group may be a $C_{12-18}$ saturated or unsaturated fatty acid group. Examples of preferred fatty acid groups include a palmitoyl group, an oleoyl group, a stearoyl group, and a linoleyl group. The phospholipid employed in the present invention is particularly preferably dioleoylphosphatidylethanolamine.

The composition of the present invention may further contain a sterol compound (e.g., cholesterol and/or cholestanol). The amount of the sterol compound is preferably 0 to 50 mol %, more preferably 16 to 50 mol %, on the basis of the total lipid content of the composition.

The amount of the aforementioned phospholipid contained in the composition of the present invention may be appropriately determined on the basis of the total lipid content of the composition. However, the ratio by mole of the compound represented by formula (I) to the phospholipid is preferably 2:3 to 16:1, more preferably 1.3:1 to 4:1.

In the composition of the present invention, (a) preferably, the ratio by mole of the compound represented by formula (I) to the phospholipid is 1.3:1 to 4:1; (b) more preferably, the ratio by mole of the compound represented by formula (I) to the phospholipid is 1.3:1 to 4:1, and the amount of the compound represented by formula (I) is 40 to 60 mol % on the basis of the total lipid content of the composition; and (c) even more preferably, the ratio by mole of the compound represented by formula (I) to the phospholipid is 1.3:1 to 4:1, the amount of the compound represented by formula (I) is 40 to 60 mol % on the basis of the total lipid content of the composition, and the amount of the sterol compound is 16 to 50 mol % on the basis of the total lipid content of the composition.

No particular limitation is imposed on the nucleic acid of interest to which the composition of the present invention is applied, and the nucleic acid may be an oligonucleotide, DNA, or RNA. Examples of the nucleic acid include short oligonucleotides such as antisense oligonucleotide, antisense DNA, antisense RNA, shRNA, siRNA, and miRNA; bioactive substances such as enzyme and cytokine; and genes encoding antisense RNA, shRNA, and siRNA.

No particular limitation is imposed on the amount of the compound represented by formula (I) contained in the composition of the present invention, so long as the amount is enough to transfect a nucleic acid into cells. The amount of the compound may be appropriately determined in consideration of, for example, the type of a nucleic acid of interest, the use of the nucleic acid, or the form of the composition. For example, in the case of a nucleic acid (200 ng) transfection, the amount of the compound represented by formula (I) contained in the composition is preferably 125 to 2,000 μmol, more preferably 250 to 1,000 μmol. In the case of siRNA transfection, the amount of the compound represented by formula (I) contained in the composition is preferably 0.1 to 10 mol, more preferably 0.5 to 2 mol against 1 mol of phosphate group. For example, in the case of 27-mer siRNA (1 mol) transfection, the amount of the compound represented by formula (I) contained in the composition is preferably 5.4 to 540 mol, more preferably 27 to 108 mol.

The composition of the present invention may be in the form of a simple mixture of the compound represented by formula (I), the phospholipid, and an optional sterol compound. Alternatively, the composition may be in the form of a lipid membrane structure produced from the compound represented by formula (I), a phospholipid, and a sterol compound.

No particular limitation is imposed on the form of the lipid membrane structure, and the lipid membrane structure may be in the form of, for example, a dry lipid mixture, an aqueous solvent dispersion, or a dry or frozen product of the dispersion.

Examples of the aqueous solvent dispersion form of the lipid membrane structure include a single-lamellar liposome, a multi-lamellar liposome, an O/W emulsion, a W/O/W emulsion, a spherical micelle, a thread-like micelle, and an amorphous layered structure. Of these, a liposome form is preferred. No particular limitation is imposed on the size of the dispersed lipid membrane structure. For example, when the lipid membrane structure is in the form of liposomes or emulsion, the structure has a particle size of 50 nm to 5 μm, whereas when the lipid membrane structure is in the form of spherical micelles, the structure has a particle size of 5 to 100 nm. When the lipid membrane structure is in the form of thread-like micelles or amorphous layered structure, the structure is preferably lamellar forms each having a thickness of 5 to 10 nm.

Next will be described methods for producing various forms of the lipid membrane structure.

(1) The lipid membrane structure in the form of dry mixture may be produced by, for example, temporarily dissolving all the components of the lipid membrane structure in an organic solvent (e.g., chloroform), and then subjecting the resultant solution to drying under reduced pressure by means of an evaporator, or to spray drying by means of a spray dryer.

(2) The lipid membrane structure in the form of aqueous solvent dispersion may be produced by adding the aforementioned dry mixture to an aqueous solvent, and then emulsifying the resultant mixture by means of, for example, an emulsifier (e.g., a homogenizer), an ultrasonic emulsifier, or a high-pressure jet emulsifier. Alternatively, the lipid membrane structure in the form of aqueous solvent dispersion may be produced through a method well-known as a liposome production method (e.g., the reverse-phase evaporation method). For control of the size of the lipid membrane structure, extrusion (extrusion typed filtration) may be carried out under high pressure by means of, for example, a membrane filter having pores of uniform size.

No particular limitation is imposed on the composition of an aqueous solvent (dispersion medium) employed. Examples of the aqueous solvent which may be employed include buffers such as phosphate buffer, citrate buffer, and phosphate buffered saline; saline; and culture media for cell culture. Such an aqueous solvent (dispersion medium), in which the lipid membrane structure can be stably dispersed, may further contain, for example, a sugar (aqueous solution thereof), or a polyhydric alcohol (aqueous solution thereof). Examples of the sugar include monosaccharides such as glucose, galactose, mannose, fructose, inositol, ribose, and xylose; disaccharides such as lactose, sucrose, cellobiose, trehalose, and maltose; trisaccharides such as raffinose and melezitose; polysaccharides such as cyclodextrin; and sugar alcohols such as erythritol, xylitol, sorbitol, mannitol, and maltitol. Examples of the polyhydric alcohol include glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, and 1,3-butylene glycol. In order to stably store the lipid membrane structure dispersed in such an aqueous solvent (dispersion medium) for a long period of time, preferably, the amount of electrolytes in the aqueous solvent (dispersion medium) is reduced to a minimum possible level, from the viewpoint of physical stability (e.g., from the viewpoint of preventing aggregation). From the viewpoint of chemical stability of lipid, preferably, the pH of the aqueous solvent (dispersion medium) is adjusted to fall within a range of 3.0 to 8.0 (i.e., from slightly acidic to around neutral), or dissolved oxygen is removed through nitrogen bubbling.

No particular limitation is imposed on the sugar or polyhydric alcohol concentration of the aqueous solvent in which the lipid membrane structure is dispersed. However, for example, the sugar (aqueous solution thereof) concentration is preferably 2 to 20% (w/v), more preferably 5 to 10% (w/v), and the polyhydric alcohol (aqueous solution thereof) concentration is preferably 1 to 5% (w/v), more preferably 2 to 2.5% (w/v). When the aqueous solvent (dispersion medium) employed is a buffer, the buffering agent concentration is preferably 5 to 50 mM, more preferably 10 to 20 mM. No particular limitation is imposed on the lipid membrane structure concentration of the aqueous solvent dispersion, but the total lipid concentration (the amounts of components of the lipid membrane structure, including di($C_{12-16}$ alkyl)dimethylammonium halide, phospholipid, and optional sterol compound) of the dispersion is preferably 0.2 to 50 mM, more preferably 1 to 10 mM.

(3) A dry or frozen product of the lipid membrane structure dispersed in any of the aforementioned aqueous solvents may be produced by subjecting the aqueous solvent dispersion of the lipid membrane structure to a common drying process (e.g., lyophilization or spray drying) or to a freezing process. When the above-produced aqueous solvent dispersion of the lipid membrane structure is further dried, the lipid membrane structure can be stored for a long period of time. When an aqueous solution containing a nucleic acid is added to the thus-dried lipid membrane structure, advantageously, the lipid mixture is effectively hydrated, and thus the nucleic acid can be effectively retained in the lipid membrane structure.

In the case where the aqueous solvent dispersion of the lipid membrane structure is lyophilized or spray-dried, when a sugar (aqueous solution thereof) (e.g., a monosaccharide such as glucose, galactose, mannose, fructose, inositol, ribose, or xylose; a disaccharide such as lactose, sucrose, cellobiose, trehalose, or maltose; a trisaccharide such as raffinose or melezitose; a polysaccharide such as cyclodextrin; or a sugar alcohol such as erythritol, xylitol, sorbitol, mannitol, or maltitol) is employed, the lipid membrane structure can be stably stored for a long period of time. In the case where the aqueous solvent dispersion of the lipid membrane structure is frozen, when any of the aforementioned sugars (aqueous solution thereof), or a polyhydric alcohol (aqueous solution thereof) (e.g., glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, or 1,3-butylene glycol) is employed, the lipid membrane structure can be stably stored for a long period of time. Such a sugar and polyhydric alcohol may be employed in combination.

The nucleic-acid-transfecting composition of the present invention may be in the form of a composition containing a nucleic acid of interest (i.e., a nucleic-acid-containing composition). Such a nucleic-acid-containing composition will next be described.

The nucleic-acid-containing composition may be in the form of a simple mixture of a compound represented by formula (I), a phospholipid, a nucleic acid, and an optional sterol compound. Alternatively, the composition may be in the form of a mixture of a nucleic acid and a lipid membrane structure formed of a compound represented by formula (I), a phospholipid, and a sterol compound. The lipid membrane structure may retain the nucleic acid. As used herein, the term "retain" refers to the case where nucleic acid is present in a lipid membrane of the lipid membrane structure, on the surface of the membrane, inside of the membrane, in a lipid layer of the structure, and/or on the surface of the lipid layer. When the lipid membrane structure is represented as microvesicles (e.g., liposomes), the nucleic acid may be encapsulated in the microvesicles.

In this case, the lipid membrane structure with nucleic acid may be in the form of, for example, a dry mixture, an aqueous solvent dispersion, or a dry or frozen product of the dispersion, as with the case of the aforementioned lipid membrane structure.

Next will be described methods for producing various forms of a lipid membrane structure with nucleic acid.

(1) The nucleic-acid-containing composition in the form of dry mixture may be produced by, for example, temporarily dissolving the components of the lipid membrane structure and a nucleic acid in an organic solvent (e.g., chloroform), and then subjecting the resultant mixture to drying under reduced pressure by means of an evaporator, or to spray drying by means of a spray dryer.

(2) The nucleic-acid-containing composition in the form of aqueous solvent dispersion containing the lipid membrane structure and a nucleic acid may be produced through several known methods. In consideration of the mode for retaining the nucleic acid in the lipid membrane structure or the properties of the mixture, the production method may be appropriately selected from among the below-described methods 2-1 to 2-5.

(2-1) Production Method 1

In production method 1, an aqueous solvent is added to the aforementioned dry mixture, and the resultant mixture is emulsified by means of, for example, an emulsifier (e.g., a homogenizer), an ultrasonic emulsifier, or a high-pressure jet emulsifier. For control of size (particle size), extrusion (extrusion typed filtration) may be carried out under high pressure by means of a membrane filter having pores of uniform size. In this production method, firstly, the lipid membrane structure and a nucleic acid must be dissolved in an organic solvent for preparing a dry mixture of the components of the lipid membrane structure and the nucleic acid. This production method is advantageous in that it can utilize to a maximum extent interaction between the components of the lipid membrane structure and the nucleic acid. Even when the lipid membrane structure has a lamellar structure, the nucleic acid can enter between multi-lamellar structures. Thus, this production method is advantageous in that the percent retention of the nucleic acid in the lipid membrane structure can be increased.

(2-2) Production Method 2

In production method 2, the components of the lipid membrane structure are temporarily dissolved in an organic solvent; the organic solvent is removed through evaporation; and an aqueous solvent containing a nucleic acid is added to the resultant dry product, followed by emulsification. For control of size (particle size), extrusion (extrusion typed filtration) may be carried out under high pressure by means of a membrane filter having pores of uniform size. This method is applicable to a nucleic acid which is difficult to dissolve in an organic solvent but can be dissolved in an aqueous solvent. This method is advantageous in that, when the lipid membrane structure is in the form of liposomes, a nucleic acid can also be retained in the internal aqueous phase of the structure.

(2-3) Production Method 3

In production method 3, an aqueous solvent containing a nucleic acid is added to the lipid membrane structure in the form of, for example, liposomes, emulsion, micelles, or lamellar structure which has already been dispersed in an aqueous solvent. This method is applicable to a water-soluble nucleic acid. In this method, a nucleic acid is added to the lipid membrane structure which has already been prepared. Therefore, when a nucleic acid of high molecular weight is employed, the nucleic acid may fail to enter inside the lipid membrane structure and may be present on (bound to) the surface of the lipid membrane structure. As has been known, when production method 3 is applied to the lipid membrane structure in the form of liposomes, a nucleic acid is sandwiched between liposome particles; i.e., a sandwich structure (generally called "complex") is formed. In this production method, since an aqueous dispersion containing only the lipid membrane structure is produced in advance, no attention must be paid to, for example, degradation of a nucleic acid during emulsification, and size (particle size) is readily controlled. Therefore, the nucleic-acid-containing composition can be readily produced through production method 3, as compared with the case of production method 1 or 2.

(2-4) Production Method 4

In production method 4, the lipid membrane structure dispersed in an aqueous solvent is dried, and an aqueous solvent containing a nucleic acid is added to the resultant dry product. Similar to the case of production method 3, production method 4 is applicable to a water-soluble nucleic acid. Production method 4 differs from production method 3 in terms of mode of presence of the lipid membrane structure and a nucleic acid. In production method 4, the lipid membrane structure is temporarily dispersed in an aqueous solvent, and the resultant dispersion is dried. At this stage of the method, the lipid membrane structure is present in the form of a solid lipid membrane fragment. In order to cause such a lipid membrane fragment to be present in a solid form, preferably, as described above, a sugar (aqueous solution thereof), more preferably sucrose or lactose (aqueous solution thereof), is added to the aqueous solvent employed. When an aqueous solvent containing a nucleic acid is added to the lipid membrane fragment present in a solid form, the lipid membrane fragment is rapidly invaded by water and hydrated, to thereby reconstitute the lipid membrane structure. In this case, the thus-reconstituted lipid membrane structure retains the nucleic acid within its structure.

In production method 3, when a nucleic acid of high molecular weight is employed, the nucleic acid fails to enter inside the lipid membrane structure and is present on (bound to) the surface of the lipid membrane structure. However, production method 4 greatly differs from production method 3 in this regard. That is, in the case of production method 4, the entirety or a portion of a nucleic acid is incorporated in the inside of the lipid membrane structure. In production method 4, since a dispersion containing only the lipid membrane structure is produced in advance, no attention must be paid to degradation of a nucleic acid during emulsification, and size (particle size) is readily controlled. Thus, the nucleic-acid-containing composition can be readily produced through production method 4, as compared with the case of production method 1 or 2. In addition, in production method 4, the lipid membrane structure is temporarily subjected to lyophilization or spray drying. Therefore, this method is advantageous in that, for example, storage stability of the final product (nucleic-acid-containing composition) is readily assured, the size (particle size) of a dry product can be restored by mixing the product with an aqueous solution of a nucleic acid, and a nucleic acid of high molecular weight is readily retained inside the lipid membrane structure.

(2-5) Other Methods

An aqueous solvent dispersion of a mixture of the lipid membrane structure and a nucleic acid may be produced through a method well known as a liposome production method (e.g., the reverse-phase evaporation method). For control of size (particle size), extrusion (extrusion typed filtration) may be carried out under high pressure by means of a membrane filter having pores of uniform size.

(3) When the aforementioned aqueous solvent dispersion of the lipid membrane structure-nucleic acid mixture is further dried, lyophilization, spray drying, or a similar technique may be employed. In this case, the aqueous solvent employed is preferably a solvent containing any of the aforementioned sugars (aqueous solution thereof), more preferably sucrose or lactose (aqueous solution thereof). When the aqueous solvent dispersion of the lipid membrane structure-nucleic acid mixture is further frozen, a common freezing technique may be employed. In this case, the aqueous solvent employed is preferably a solvent containing a sugar (aqueous solution thereof) or a polyhydric alcohol (aqueous solution thereof).

The thus-produced composition of the present invention realizes an effective nucleic acid transfection into cells. Therefore, the composition of the present invention can be employed as a nucleic-acid-transfecting agent (e.g., a nucleic-acid-transfecting reagent or drug). When the nucleic-acid-containing composition of the present invention is employed in vitro, for example, the composition may be added to a suspension containing a target cell, or the target cell may be cultured in a medium containing the composition, to thereby transfect the nucleic acid into the target cell. When the nucleic-acid-containing composition of the present invention is employed in vivo, the composition may be administered to a human or a non-human animal. The composition may be orally or parenterally administered. The oral dosage form may be a generally known one; for example, tablet, powder, or granules. The parenteral dosage form may be a generally known one; for example, injection, eye drop, ointment, or suppository. Parenteral administration is preferred, with injection being particularly preferred. Preferably, intravenous injection or local injection into a target cell or organ is carried out.

The nucleic-acid-transfecting composition of the present invention can be employed in a screening method for selecting a substance which enhances or inhibits expression of a target nucleic acid, the method including the following steps (1) to (3):

(1) a step of bringing a test substance into contact with a cell into which a target nucleic acid has been transfected;

(2) a step of determining the level of expression of the target nucleic acid in the cell which has been brought into contact with the test substance; and (3) a step of selecting a test substance showing an expression level as determined in (2) above that is higher or lower than the level of expression of the target nucleic acid in a control cell. Specifically, the composition can be employed for transfection of the target nucleic acid into the cell and/or for exposure (introduction) of the cell to the test substance.

Examples of the target nucleic acid include disease-associated genes and plasmid DNA containing such a gene. Examples of the test substance include low-molecular-weight compounds having a molecular weight of less than 10,000, preferably 100 to 2,000, and short nucleotides such as antisense oligonucleotide, antisense DNA, antisense RNA, shRNA, siRNA, and miRNA.

The level of expression of the nucleic acid may be determined through, for example, a known technique such as northern blotting, RT-PCR, or quantitative PCR, or a determination method employing a DNA array.

Examples of the control cell include a cell which is not exposed to the test substance, and a cell into which a short nucleotide or predetermined substance that does not affect the target nucleic acid has been transfected.

EXAMPLES

The present invention will next be described by way of examples, which should not be construed as limiting the invention thereto.

Example 1

N-(α-Trimethylammonioacetyl)-didodecyl-D-glutamate chloride (product name: DC-3-12D, product of Sogo Pharmaceutical Co., Ltd.) (40 mol %), cholesterol (product of Waka Pure Chemical Industries, Ltd.) (30 mol %), and dioleoylphosphatidylethanolamine (DOPE, product of NOF corporation) (30 mol %) were dissolved in chloroform, and the resultant solution was dried to solid under reduced pressure, to thereby prepare a lipid mixture. A 9% sucrose solution was added to the lipid mixture, and the mixture was subjected to indirect ultrasonic irradiation by means of a sonicator under heating at 65° C., to thereby yield a crude liposome dispersion having a DC-3-12D concentration of 2.5 mM. Subsequently, two filters (pore size: 0.22 μm) were placed in an extruder so that the filters were overlapped with each other, and the crude liposome dispersion was subjected to extrusion (extrusion typed filtration) under heating at about 65° C. and pressurized conditions, so as to prepare liposomes having a uniform particle size. Thereafter, in a manner similar to that described above, the resultant dispersion was subjected to extrusion by use of a filter (pore size: 0.1 μm), to thereby yield a dispersion of empty liposomes. The liposome dispersion was dispensed into 2-mL vials (1 mL each), followed by lyophilization, to thereby yield lyophilized liposomes (Preparation Example 1). The mean particle size and zeta potential of the liposomes of Preparation Example 1 were determined by means of NICOMP 380ZLS (product of Particle Sizing System). The results are shown in Table 2.

Example 2

The procedure of Example 1 was repeated, except that N-(α-trimethylammonioacetyl)-didodecyl-D-glutamate chloride was replaced with N-α-trimethylammonioacetyl)-didodecyl-L-glutamate chloride (product name: DC-3-12L, product of Sogo Pharmaceutical Co., Ltd.), to thereby yield lyophilized liposomes (Preparation Example 2). The mean particle size and zeta potential of the liposomes were determined in a manner similar to that described in Example 1. The results are shown in Table 2.

Example 3

The procedure of Example 1 was repeated, except that N-(α-trimethylammonioacetyl)-didodecyl-D-glutamate chloride was replaced with N-(α-trimethylammonioacetyl)-dioctadecyl-D-glutamate chloride (product name: DC-3-18D, product of Sogo Pharmaceutical Co., Ltd.), to thereby yield lyophilized liposomes (Preparation Example 3). The mean particle size and zeta potential of the liposomes were determined in a manner similar to that described in Example 1. The results are shown in Table 2.

Example 4

The procedure of Example 1 was repeated, except that N-(α-trimethylammonioacetyl)-didodecyl-D-glutamate chloride was replaced with N-ω-trimethylammoniodecanoyl-dihexadecyl-D-glutamate bromide (product name: DC-12-16D, product of Sogo Pharmaceutical Co., Ltd.), to thereby yield lyophilized liposomes (Preparation Example 4). The mean particle size and zeta potential of the liposomes were determined in a manner similar to that described in Example 1. The results are shown in Table 2.

Example 5

The procedure of Example 1 was repeated, except that N-(α-trimethylammonioacetyl)-didodecyl-D-glutamate chloride was replaced with N-ω-trimethylammoniodecanoyl-dihexadecyl-L-glutamate bromide (product name: DC-12-16L, product of Sogo Pharmaceutical Co., Ltd.), to thereby yield lyophilized liposomes (Preparation Example 5). The mean particle size and zeta potential of the liposomes were determined in a manner similar to that described in Example 1. The results are shown in Table 2.

Example 6

The procedure of Example 1 was repeated, except that N-(α-trimethylammonioacetyl)-didodecyl-D-glutamate chloride was replaced with N-(α-trimethylammonioacetyl)-dioleyl-D-glutamate chloride (the compound of Production Example 1 of JP-A-1994-200336, hereinafter abbreviated as "DC-3-18:1D"), to thereby yield lyophilized liposomes (Preparation Example 6). The mean particle size and zeta potential of the liposomes were determined in a manner similar to that described in Example 1. The results are shown in Table 2.

Table 1 shows compositions of the liposomes of Preparation Examples 1 to 6.

TABLE 1

|  | DOPE (%) | Cholesterol (%) | DC-3-12D (%) | DC-3-12L (%) | DC-3-18D (%) | DC-12-16L (%) | DC-12-16D (%) | DC-3-18:1D (%) |
|---|---|---|---|---|---|---|---|---|
| Preparation Example 1 | 30 | 30 | 40 | 0 | 0 | 0 | 0 | 0 |
| Preparation Example 2 | 30 | 30 | 0 | 40 | 0 | 0 | 0 | 0 |
| Preparation Example 3 | 30 | 30 | 0 | 0 | 40 | 0 | 0 | 0 |
| Preparation Example 4 | 30 | 30 | 0 | 0 | 0 | 40 | 0 | 0 |
| Preparation Example 5 | 30 | 30 | 0 | 0 | 0 | 0 | 40 | 0 |
| Preparation Example 6 | 30 | 30 | 0 | 0 | 0 | 0 | 0 | 40 |

TABLE 2

|  | Mean particle size (nm) | Zeta potential (mV) |
|---|---|---|
| Preparation Example 1 | 110 | 22 |
| Preparation Example 2 | 132 | 24 |
| Preparation Example 3 | 145 | 24 |
| Preparation Example 4 | 118 | 24 |
| Preparation Example 5 | 123 | 18 |
| Preparation Example 6 | 96 | 12 |

Test Example 1

Test for Transfection of Nucleic Acid into CHO Cells

An aqueous solution of siRNA having the below-described sequences (1 pmol/μL) was 6.25-fold diluted with an F12 Ham medium, to thereby prepare a siRNA-diluted solution. Separately, the lyophilized liposome product of Preparation Example 1 was reconstituted with an appropriate amount of water to give a solution having a DC-3-12D concentration of about 1 mM.

Sense:
5'-ACAUCACGUACGCGGAAUACUUCGA-AG-3' (SEQ ID NO: 1)

Antisense:
3'-UA-UGUAGUGCAUGCGCCUUAUGAAGCU-5' (SEQ ID NO: 2)

The thus-obtained solution was 20.8- or 125-fold diluted with an F-12 HAM medium. Each of the thus-diluted solutions was added to and mixed with an equiamount of the siRNA-diluted solution, to thereby form a siRNA/liposome complex. In this case, the ratio of the amount of DC-3-12D-derived cations to the amount of siRNA-derived anions is about 6 (for the case of 20.8-fold dilution) or about 1 (for the case of 125-fold dilution). Subsequently, the resultant solution was added to and mixed with an equiamount of a 20%-FBS-containing F-12 HAM medium, to thereby prepare a siRNA/liposome-complex-containing medium. Medium for CHO (pMAM-luc) cells (JCRB0136.1, obtained from Human Science Research Resources Bank) was replaced with the siRNA/liposome-complex-containing medium, to thereby initiate transfection. After culturing at 37° C. and 5% $CO_2$ for about 41 hours, the medium was replaced with an F-12 HAM medium containing 1 μM dexamethasone and 10% FBS. After culturing at 37° C. and 5% $CO_2$ for about six to about eight hours, cells were observed under a microscope, and cytotoxicity was evaluated according to the following scores (−: cells cover about 85 to about 100% of the field of view, and no trace of damage due to toxicity is observed; ±: cells cover about 85 to about 100% of the field of view, but some trace of damage due to toxicity is observed; +: cells cover about 70 to about 80% of the field of view; ++: cells cover about 50 to about 70% of the field of view; and +++: cells cover only less than about 50% of the field of view). The results are shown in Table 3. After removal of the medium, the cells were washed with PBS. Subsequently, the cells were lysed with PLB, and then luciferase activity was determined. For a control, the above-described experiment was repeated, except that water was employed in place of the siRNA solution. The experiment was carried out for the lyophilized liposomes of Preparation Examples 2 to 6 in the same manner as in the case of Preparation Example 1. Percent knockdown (%) was calculated on the basis of the following formula (1). The results are shown in Table 3.

100×(luciferase activity in the presence of siRNA)/
(luciferase activity in the absence of siRNA)    Formula (1)

Separately, for a positive control, percent knockdown was evaluated by use of Lipofectamine 2000 (trade name: product of Invitrogen).

The siRNA solution (1 pmol/μL) was 2.5-fold diluted with an F-12 HAM medium, to thereby prepare a siRNA-diluted solution. Separately, Lipofectamine 2000 (trade name: product of Invitrogen) was 50-fold diluted with an F-12 HAM medium. The thus-diluted solution was added to an equiamount of the siRNA-diluted solution, to thereby prepare a siRNA/Lipofectamine 2000-containing medium. The thus-prepared medium (20 μL) was added to separately cultured CHO (pMAM-luc) cells (medium amount: 100 μL), to thereby initiate transfection. After culturing at 37° C. and 5% $CO_2$ for about 41 hours, the medium was replaced with an F12-Ham medium containing 1 μM dexamethasone and 10% FBS. After culturing at 37° C. and 5% $CO_2$ for about seven hours, cells were observed under a microscope, and cytotoxicity was evaluated according to the aforementioned scores. After removal of the medium, the cells were washed with PBS(−). Subsequently, the cells were lysed with 1×PLB, and then luciferase activity was determined. For a control, the above-described experiment was repeated, except that water was employed in place of the siRNA solution, and percent knockdown (%) was calculated on the basis of formula (1). As a result, cytotoxicity was found to be low (score: −), but white spots were observed in the cells. Percent knockdown was found to be 38%.

Test Example 2

Test for Transfection of Nucleic Acid into HeLa Cells

An aqueous solution of siRNA having the below-described sequences (1 pmol/μL) was 6.25-fold diluted with a Dulbecco's modified Eagle's medium (hereinafter abbreviated as a "DMEM medium"), to thereby prepare a siRNA-diluted solution. Separately, the lyophilized liposome product of Preparation Example 1 was reconstituted with an appropriate amount of water to give a solution having a DC-3-12D concentration of about 1 mM.

Sense:
5'-ACAUCACUUACGCUGAGUACUUCGA-AG-3' (SEQ ID NO: 3)

Antisense:
3'-UA-UGUAGUGAAUGCGACUCAUGAAGCU-5' (SEQ ID NO: 4)

The thus-obtained solution was 28.8-, 115-, or 215-fold diluted with a DMEM medium. Each of the thus-diluted solutions was added to and mixed with an equiamount of the siRNA-diluted solution, to thereby form a siRNA/liposome complex. In this case, the ratio of the amount of DC-3-12D-derived cations to the amount of siRNA-derived anions is about 4 (for the case of 28.8-fold dilution), about 1 (for the case of 115-fold dilution), or about 0.5 (for the case of 215-fold dilution). Subsequently, the resultant solution was added to and mixed with an equiamount of a 20%-FBS-containing DMEM medium, to thereby prepare a siRNA/liposome-complex-containing medium. Medium for cells of the NFAT Reporter HeLa Stable Cell Line (product of Panomics) was replaced with the siRNA/liposome-complex-containing medium, to thereby initiate transfection. After culturing at 37° C. and 5% $CO_2$ for about 18 hours, the medium was replaced with a DMEM medium containing 10 ng/mL PMA, 0.5 μM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. The results are shown in Table 3. After removal of the medium, the cells were washed with PBS. Subsequently, the cells were lysed with PLB, and then luciferase activity was determined. For a control, the above-described experiment was repeated, except that water was employed in place of the siRNA solution. The experiment was carried out for the lyophilized liposomes of Preparation Examples 2 to 6 in the same manner as in the case of Preparation Example 1. Percent knockdown (%) was calculated on the basis of formula (1). The results are shown in Table 3.

Separately, for a positive control, percent knockdown was evaluated by use of Lipofectamine 2000 (trade name: product of Invitrogen).

The siRNA solution (1 pmol/μL) was 2.5-fold diluted with a DMEM medium, to thereby prepare a siRNA-diluted solution. Separately, Lipofectamine 2000 was 100-fold diluted with a DMEM medium. The thus-diluted solution was added to an equiamount of the siRNA-diluted solution, to thereby prepare a siRNA/Lipofectamine 2000-containing medium. The thus-prepared medium (20 μL) was added to a medium (100 μL) of separately cultured NFAT Reporter HeLa Stable Cell Line (product of Panomics), to thereby initiate transfection. After culturing at 37° C. and 5% $CO_2$ for about 18 hours, the medium was replaced with a DMEM medium containing 10 ng/mL PMA, 0.5 μM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution, and percent knockdown (%) was calculated on the basis of formula (1). As a result, cytotoxicity was found to be low (score: −), but white spots were observed in the cells. Percent knockdown was found to be 9%.

TABLE 3

| | Cells | | | | |
|---|---|---|---|---|---|
| | CHO | | HeLa | | |
| Cation/Anion | 1 | 6 | 0.5 | 1 | 4 |
| Preparation Example 1 | 93 | 53 | 24 | 12 | 5 |
| | − | − | − | − | ++ |
| Preparation Example 2 | 79 | 55 | 11 | 7 | 4 |
| | − | − | − | − | ++ |
| Preparation Example 3 | 100 | 91 | 77 | 91 | 33 |
| | − | − | − | − | − |
| Preparation Example 4 | 125 | 125 | 96 | 73 | 57 |
| | − | + | − | − | ± |
| Preparation Example 5 | 109 | 129 | 97 | 80 | 67 |
| | − | − | − | − | − |
| Preparation Example 6 | 12 | 11 | 10 | 6 | 8 |
| | − | + | − | + | ++ |

Upper: percent knockdown (%),
Lower: cytotoxicity score

As shown in Table 3, the composition of Preparation Example 6 (i.e., the composition of the present invention) exhibited particularly excellent nucleic-acid-transfecting performance (percent knockdown) and low cytotoxicity. As compared with Lipofectamine 2000, the composition of the present invention exhibited high nucleic-acid-transfecting performance and low cytotoxicity regardless of cell types (the nucleic-acid-transfecting performance of Lipofectamine 2000 was high for HeLa cells, but insufficient for CHO cells). Thus, the compound represented by formula (I) in which $R^1$ and $R^2$ are alkenyl groups was found to exhibit excellent nucleic-acid-transfecting performance and low cytotoxicity.

Example 7

In a manner similar to that described in Preparation Example 6, lyophilized liposomes shown in Table 4 were prepared (Preparation Examples 7 to 22). In a manner similar to that described in Example 1, the mean particle size and zeta potential of the liposomes were determined. The results are shown in Table 5.

TABLE 4

| | DOPE (%) | Cholesterol (%) | DC-3-18:1D (%) |
|---|---|---|---|
| Preparation Example 7 | 0 | 50 | 50 |
| Preparation Example 8 | 10 | 50 | 40 |
| Preparation Example 9 | 20 | 50 | 30 |
| Preparation Example 10 | 30 | 50 | 20 |
| Preparation Example 11 | 0 | 32 | 68 |
| Preparation Example 12 | 15 | 32 | 53 |
| Preparation Example 13 | 45 | 32 | 23 |
| Preparation Example 14 | 5 | 16 | 79 |
| Preparation Example 15 | 24 | 16 | 60 |
| Preparation Example 16 | 42 | 16 | 42 |
| Preparation Example 17 | 63 | 16 | 21 |
| Preparation Example 18 | 20 | 0 | 80 |
| Preparation Example 19 | 28.6 | 0 | 71.4 |
| Preparation Example 20 | 40 | 0 | 60 |
| Preparation Example 21 | 60 | 0 | 40 |
| Preparation Example 22 | 80 | 0 | 20 |

TABLE 5

| | Mean particle size (nm) | Zeta potential (mV) |
|---|---|---|
| Preparation Example 7 | 123 | 20 |
| Preparation Example 8 | 131 | 17 |
| Preparation Example 9 | 88 | 15 |
| Preparation Example 10 | 85 | 24 |
| Preparation Example 11 | 112 | 15 |
| Preparation Example 12 | 116 | 16 |
| Preparation Example 13 | 113 | 20 |
| Preparation Example 14 | 84 | 16 |
| Preparation Example 15 | 89 | 17 |
| Preparation Example 16 | 129 | 19 |
| Preparation Example 17 | 150 | 20 |
| Preparation Example 18 | 108 | 19 |
| Preparation Example 19 | 73 | 15 |
| Preparation Example 20 | 115 | 19 |
| Preparation Example 21 | 87 | 20 |
| Preparation Example 22 | 146 | 25 |

Test Example 3

Test for Transfection of Nucleic Acid into CHO Cells

The siRNA solution (1 pmol/μL) employed in Test Example 1 was 6.25-fold diluted with an F-12 HAM medium, to thereby prepare a siRNA-diluted solution. Separately, the lyophilized liposome product of each of Preparation Examples 6 to 21 was reconstituted with an appropriate amount of water to give a solution having a DC-3-18:1D concentration of about 1 mM. The thus-obtained solution was 14.4-, 19.2-, or 56.7-fold diluted with an F-12 HAM medium. Each of the thus-diluted solutions was added to and mixed with an equiamount of the siRNA-diluted solution, to thereby form a siRNA/liposome complex. In this case, the ratio of the amount of DC-3-18:1D-derived cations to the amount of siRNA-derived anions is about 8 (for the case of 14.4-fold dilution), about 6 (for the case of 19.2-fold dilution), or about 2 (for the case of 56.7-fold dilution). Subsequently, the resultant solution was added to and mixed with an equiamount of a 20%-FBS-containing F-12 HAM medium, to thereby prepare a siRNA/liposome-complex-containing medium. Medium for CHO (pMAM-luc) cells (JCRB0136.1, obtained from Human Science Research Resources Bank) was replaced with the siRNA/liposome-complex-containing medium, to thereby initiate transfection. After culturing at 37° C. and 5% $CO_2$ for about 41 hours, the medium was replaced with an F-12 HAM medium containing 1 μM dexamethasone and 10% FBS. After culturing at 37° C. and 5% $CO_2$ for about six to about eight hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution. Percent knockdown (%) was calculated on the basis of formula (1). The results are shown in Table 6.

Separately, for a positive control, Lipofectamine 2000 (trade name: product of Invitrogen) was employed, and, in a manner similar to that described in Test Example 1, cytotoxicity was evaluated according to the aforementioned scores, and percent knockdown (%) was calculated. As a result, cytotoxicity was found to be low (score: −), but white spots were observed in the cells. Percent knockdown was found to be 54%.

TABLE 6

| Preparation Example | DOPE (%) | Cholesterol (%) | DC-3-18:1D (%) | DC-3-18:1D/ DOPE | DC-3-18:1D concentration (pmol/well) | | |
|---|---|---|---|---|---|---|---|
| | | | | | 432 | 1296 | 1728 |
| 6 | 30 | 30 | 40 | 1.33 | 13 | 9 | 13 |
| | | | | | − | − | ± |
| 7 | 0 | 50 | 50 | — | 55 | 70 | 67 |
| | | | | | − | − | − |
| 8 | 10 | 50 | 40 | 4.00 | 20 | 6 | 10 |
| | | | | | − | − | − |
| 9 | 20 | 50 | 30 | 1.50 | 12 | 11 | 14 |
| | | | | | − | − | + |
| 10 | 30 | 50 | 20 | 0.67 | 26 | 16 | 18 |
| | | | | | − | − | − |
| 11 | 0 | 28.6 | 71.4 | — | 69 | 78 | 66 |
| | | | | | − | − | − |
| 12 | 15 | 32 | 53 | 3.53 | 19 | 7 | 9 |
| | | | | | − | − | + |
| 13 | 45 | 32 | 23 | 0.51 | 26 | 20 | 19 |
| | | | | | − | − | − |
| 14 | 5 | 16 | 79 | 15.80 | 55 | 36 | 28 |
| | | | | | − | − | − |
| 15 | 24 | 16 | 60 | 2.50 | 19 | 9 | 10 |
| | | | | | − | − | ++ |
| 16 | 42 | 16 | 42 | 1.00 | 15 | 14 | 13 |
| | | | | | − | − | + |
| 17 | 63 | 16 | 21 | 0.33 | 47 | 32 | 23 |
| | | | | | − | − | − |
| 18 | 20 | 0 | 80 | 4.00 | 73 | 40 | 25 |
| | | | | | − | − | − |
| 19 | 28.6 | 0 | 71.4 | 2.50 | 38 | 27 | 25 |
| | | | | | − | − | ± |
| 20 | 40 | 0 | 60 | 1.50 | 16 | 17 | 14 |
| | | | | | − | − | + |
| 21 | 60 | 0 | 40 | 0.67 | 14 | 11 | 13 |
| | | | | | − | ± | ++ |

Upper: percent knockdown (%),
Lower: cytotoxicity score

Test Example 4

Test for Transfection of Nucleic Acid into HeLa Cells

The siRNA solution (1 pmol/μL) employed in Test Example 2 was 6.25-fold diluted with a DMEM medium, to thereby prepare a siRNA-diluted solution. Separately, the lyophilized liposome product of each of Preparation Examples 6 to 21 was reconstituted with an appropriate amount of water to give a solution having a DC-3-18:1D concentration of about 1 mM. The thus-obtained solution was 28.8-, 57.7-, 115-, or 500-fold diluted with a DMEM medium. Each of the thus-diluted solutions was added to and mixed with an equiamount of the siRNA-diluted solution, to thereby form a siRNA/liposome complex. Subsequently, the resultant solution was added to and mixed with an equiamount of a 20%-FBS-containing DMEM medium, to thereby prepare a siRNA/liposome-complex-containing medium. Medium for cells of the NFAT Reporter HeLa Stable Cell Line (product of Panomics) was replaced with the siRNA/liposome-complex-containing medium, to thereby initiate transfection. After culturing at 37° C. and 5% $CO_2$ for about 18 hours, the medium was replaced with a DMEM medium containing 10 ng/mL PMA, 0.5 μM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS. Subsequently, the cells were lysed with PLB, and then luciferase activity was determined. For a control, the above-described experiment was repeated, except that water was employed in place of the siRNA solution. Percent knockdown (%) was calculated on the basis of formula (1). The results are shown in Table 7.

Separately, for a positive control, Lipofectamine 2000 (trade name: product of Invitrogen) was employed, and, in a manner similar to that described in Test Example 2, cytotoxicity was evaluated according to the aforementioned scores, and percent knockdown (%) was calculated. As a result, cytotoxicity was found to be low (score: −), but white spots were observed in the cells. Percent knockdown was found to be 10%.

TABLE 7

| Preparation Example | DOPE (%) | Cholesterol (%) | DC-3-18:1D (%) | DC-3-18:1D/ DOPE | DC-3-18:1D concentration (pmol/well) 54 | 216 | 432 | 864 |
|---|---|---|---|---|---|---|---|---|
| 6 | 30 | 30 | 40 | 1.33 | 10 / − | 6 / − | 4 / − | 19 / ++ |
| 7 | 0 | 50 | 50 | — | 53 / − | 22 / − | 13 / − | 10 / ++ |
| 8 | 10 | 50 | 40 | 4.00 | 15 / − | 7 / − | 5 / − | 9 / +++ |
| 9 | 20 | 50 | 30 | 1.50 | 22 / − | 6 / − | 4 / + | 15 / +++ |
| 10 | 30 | 50 | 20 | 0.67 | 76 / − | 56 / − | 70 / ± | 20 / ++ |
| 11 | 0 | 32 | 68 | — | 39 / − | 26 / − | 15 / − | 20 / − |
| 12 | 15 | 32 | 53 | 3.53 | 19 / − | 5 / − | 4 / − | 9 / +++ |
| 13 | 45 | 32 | 23 | 0.51 | 86 / − | 65 / − | 83 / − | 22 / − |
| 14 | 5 | 16 | 79 | 15.80 | 26 / − | 16 / − | 7 / ± | 18 / + |
| 15 | 24 | 16 | 60 | 2.50 | 17 / − | 7 / − | 4 / ± | 7 / +++ |
| 16 | 42 | 16 | 42 | 1.00 | 13 / − | 8 / − | 5 / ± | 8 / + |
| 17 | 63 | 16 | 21 | 0.33 | 68 / − | 97 / − | 70 / − | 56 / − |
| 18 | 20 | 0 | 80 | 4.00 | 20 / − | 5 / − | 5 / + | 13 / ++ |
| 19 | 28.6 | 0 | 71.4 | 2.50 | 87 / − | 19 / − | 21 / − | 7 / ± |
| 20 | 40 | 0 | 60 | 1.50 | 10 / − | 6 / − | 5 / ± | 8 / +++ |
| 21 | 60 | 0 | 40 | 0.67 | 12 / − | 5 / − | 14 / − | 9 / + |

Upper: percent knockdown (%),
Lower: cytotoxicity score

As shown in Tables 6 and 7, the compositions of Preparation Examples 6, 8, 9, 12, 15, 18, 19, and 20 (i.e., the compositions of the present invention) exhibited excellent nucleic-acid-transfecting performance and low cytotoxicity. Particularly, the compositions of Preparation Examples 6, 8, 12, 15, and 20 were found to be preferable, and the compositions of Preparation Examples 6, 8, 12, and 15 were found to be more preferable.

These data indicate that when the concentrations of, for example, the compound represented by formula (I), phospholipid, and cholesterol employed in the present invention are appropriately determined, the resultant nucleic-acid-transfecting composition exhibits more excellent performance in terms of transfection of nucleic acid and cytotoxicity.

Test Example 5

Test for Transfection of Nucleic Acid into HeLa Cells

Nucleic-acid-encapsulated liposomes and nucleic-acid-complex-form liposomes were compared in terms of nucleic-acid-transfecting performance.

(1) Evaluation of Nucleic-Acid-Encapsulated Liposomes

The lyophilized liposome product of Preparation Example 6 was reconstituted with the aqueous siRNA solution employed in Test Example 2 (34.3 pmol/µL, 18.5 pmol/µL, or 4.6 pmol/µL) to give a solution having a DC-3-18:1D concentration of about 1 mM, thereby forming siRNA-encapsulated liposomes. The thus-obtained solution was 428.6-, 230.8-, or 57.7-fold diluted with a DMEM medium. Each of the thus-diluted solutions was added to and mixed with an equiamount of a 20%-FBS-containing DMEM medium, to thereby prepare a siRNA-encapsulated-liposomes-containing medium. Medium for cells of the NFAT Reporter HeLa Stable Cell Line (product of Panomics) was replaced with the siRNA-encapsulated-liposomes-containing medium, to thereby initiate transfection. After culturing at 37° C. and 5% $CO_2$ for about 18 hours, the medium was replaced with a DMEM medium containing 10 ng/mL PMA, 0.5 µM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution. Percent knockdown (%) was calculated on the basis of formula (1). The results are shown in Table 8.

(2) Evaluation of Nucleic-Acid-Complex-Form Liposomes

The aqueous siRNA solution employed above in (1) (1 pmol/µL) was diluted with a DMEM medium, to thereby prepare a DMEM medium containing siRNA (80.2 pmol/µL, 80.3 pmol/µL, or 81.4 pmol/µL). Separately, the lyophilized liposome product of Preparation Example 6 was reconstituted with an appropriate amount of water to give a solution having a DC-3-18:1D concentration of about 1 mM. The thus-obtained solution was 428.6-, 230.8-, or 57.7-fold diluted with the DMEM medium containing siRNA (80.2 pmol/µL, 80.3 pmol/µL, or 81.4 pmol/µL), to thereby yield siRNA-complex-form liposomes. Each of the thus-diluted solutions was added to and mixed with an equiamount of a 20%-FBS-containing DMEM medium, to thereby prepare a medium containing siRNA-complex-form liposomes. Medium for cells of the NFAT Reporter HeLa Stable Cell Line (product of Panomics) was replaced with the siRNA-complex-liposomes-containing medium, to thereby initiate transfection. After culturing at 37° C. and 5% $CO_2$ for about 18 hours, the medium was replaced with a DMEM medium containing 10 ng/mL PMA, 0.5 µM calcium ionophore A23187, and 10% FBS. After culturing at 37° C. and 5% $CO_2$ for about six hours, cells were observed under a microscope, and cytotoxicity was evaluated according to the aforementioned scores in a manner similar to that described in Test Example 1. After removal of the medium, the cells were washed with PBS(−). Subsequently, the cells were lysed with 1×PLB, and then luciferase activity was determined. For a control, the above-described experiment was repeated, except that water was employed in place of the siRNA solution. Percent knockdown (%) was calculated on the basis of formula (1). The results are shown in Table 8.

TABLE 8

| Amount of liposomes added | Percent knockdown (%) | |
|---|---|---|
| (µL/well) | Encapsulated-form | Complex-form |
| 0.108 | 11 | 19 |
| 0.216 | 7 | 11 |
| 0.432 | 3 | 4 |

As shown in Table 8, as compared with the case of the complex-form liposomes, the siRNA-encapsulated liposomes obtained by adding the siRNA solution directly to the lyophilized liposomes exhibited high knockdown effect regardless of the amount of the liposomes added.

Industrial Applicability

The composition of the present invention exhibits low cytotoxicity and realizes an effective nucleic acid transfection into cells. Therefore, the composition is useful as a nucleic-acid-transfecting agent (e.g., a nucleic-acid-transfecting reagent or drug).

The invention claimed is:

1. A composition, comprising:
 a phospholipid; and N-(α-trimethylammonioacetyl)-dioleyl-D-glutamate chloride;
 wherein the composition is suitable for transfecting a nucleic acid into a cell.

2. The composition of claim 1, further comprising:
 at least one selected from the group consisting of cholesterol and cholestanol, in an amount of 0 to 50 mol% based on a total lipid content of the composition.

3. The composition of claim 1, wherein the amount of N-(α-trimethylammonioacetyl)-dioleyl-D-glutamate chloride is 40 to 60 mol% based on a total lipid content of the composition.

4. The composition of claim 1, wherein a ratio by mole of N-(α-trimethylammonioacetyl)-dioleyl-D-glutamate chloride to the phospholipid is 2:3 to 16:1.

5. The composition of claim 1, wherein the phospholipid is at least one species selected from the group consisting of phosphatidylethanolamine, phosphatidylcholine, phosphatidylserine, phosphatidylinositol, phosphatidylglycerol, cardiolipin, sphingomyelin, plasmalogen, and phosphatidic acid.

6. The composition of claim 1, wherein the phospholipid is phosphatidylethanolamine.

7. The composition of claim 1, wherein the phospholipid is dioleoylphosphatidylethanolamine.

8. A composition, comprising:
 N-(α-trimethylammonioacetyl)-dioleyl-D-glutamate chloride;
 dioleoylphosphatidylethanolamine; and
 cholesterol,
 wherein the composition is suitable for transfecting a nucleic acid into a cell.

9. The composition of claim 1, further comprising a nucleic acid.

10. The composition of claim 9, wherein the nucleic acid is a short oligonucleotide.

11. The composition of claim 1, in the form of a lipid membrane structure.

12. The composition of claim 1, in the form of a liposome.

13. The composition of claim 1, which is a lyophilized product.

14. A method for transfecting a nucleic acid into a cell, comprising:
 applying the composition of claim 9 to a cell in vitro or in vivo.

* * * * *